(12) United States Patent
Pham Duc et al.

(10) Patent No.: US 9,919,989 B2
(45) Date of Patent: Mar. 20, 2018

(54) SEPARATION SEQUENCE FOR HYDROCARBONS FROM A GENTLE THERMAL CLEAVAGE

(75) Inventors: Tuat Pham Duc, Penzberg (DE); Gunther Schmidt, Deisenhofen (DE); Holger Schmigalle, Wolfratshausen (DE); Naree Schmigalle, legal representative, Wolfratshausen (DE); Stefanie Walter, Seehausen (DE)

(73) Assignee: LINDE AKTIENGESELLSCHAFT, Munich (DE)

( * ) Notice: Subject to any disclaimer, the term of this patent is extended or adjusted under 35 U.S.C. 154(b) by 698 days.

(21) Appl. No.: 14/238,394

(22) PCT Filed: Aug. 2, 2012

(86) PCT No.: PCT/EP2012/003299
§ 371 (c)(1),
(2), (4) Date: Sep. 4, 2014

(87) PCT Pub. No.: WO2013/020675
PCT Pub. Date: Feb. 14, 2013

(65) Prior Publication Data
US 2015/0025292 A1     Jan. 22, 2015

(30) Foreign Application Priority Data

Aug. 11, 2011    (DE) .......................... 10 2011 110 003
Nov. 17, 2011    (EP) ..................................... 11009115

(51) Int. Cl.
*C07C 7/00*       (2006.01)
*C07C 7/04*       (2006.01)
(Continued)

(52) U.S. Cl.
CPC ................ *C07C 7/005* (2013.01); *C07C 7/04* (2013.01); *C07C 7/11* (2013.01); *C10G 70/04* (2013.01)

(58) Field of Classification Search
CPC .. C07C 7/005; C07C 7/04; C07C 7/11; C07C 11/02; C10G 70/04
See application file for complete search history.

(56) References Cited

U.S. PATENT DOCUMENTS 4,695,662 A    9/1987   Vora et al.
6,033,555 A *   3/2000   Chen .......................... C07C 4/02
                                                             208/113

(Continued)

FOREIGN PATENT DOCUMENTS

CN         101050160 A     10/2007
CN         101445419 A     6/2009
(Continued)

OTHER PUBLICATIONS

Dünnebier et al. ("Optimal design of thermally coupled distillation columns." Industrial & engineering chemistry research 38.1 (1999): 162-176).*

(Continued)

*Primary Examiner* — Brian A McCaig
*Assistant Examiner* — Jason Y Chong
(74) *Attorney, Agent, or Firm* — Millen White Zelano & Branigan, PC

(57) ABSTRACT

The invention describes a method for separating hydrocarbons in an installation for generating hydrocarbons from a hydrocarbon-containing charge by cleavage. The product gas of the cleavage, which contains gaseous hydrocarbons, is compressed, dried, and supplied as charge material into a separation stage (a front end C3/C4 separation). The front end C3/C4 separation comprises a C4 absorber and a depro- (Continued)

panizer. A hydrocarbon fraction consisting of hydrocarbons having a maximum of 3 carbon atoms is obtained as a gaseous overhead product of the C4 absorber. A liquid hydrocarbon fraction consisting of hydrocarbons having at least 4 carbon atoms is obtained as a bottom product of the depropanizer. The front end C3/C4 separation comprises an additional process technological C2/C4 separation stage is arranged between the C4 absorber and the depropanizer.

17 Claims, 2 Drawing Sheets

(51) Int. Cl.
  *C07C 7/11* (2006.01)
  *C10G 70/04* (2006.01)
  *B01D 3/14* (2006.01)

(56) References Cited

U.S. PATENT DOCUMENTS

| | | |
|---|---|---|
| 7,057,083 B2 | 6/2006 | Xu et al. |
| 7,956,231 B2 | 6/2011 | Duc et al. |
| 2005/0101816 A1 | 5/2005 | Xu et al. |
| 2007/0219401 A1 | 9/2007 | Duc et al. |

FOREIGN PATENT DOCUMENTS

| | | |
|---|---|---|
| CN | 101993322 A | 3/2011 |
| DE | 102006010519 A1 | 9/2007 |
| DE | 102009038456 A1 | 3/2011 |

OTHER PUBLICATIONS

Price ("Distillation I: Principles", http://facstaff.cbu.edu/rprice/lectures/distill.html, Feb. 13, 2003).*
Wison Shanghai Chemical Engine, "Method for separating lower hydrocarbon containing light gas by combining distillation and solvent absorption," Espancenet, Publication Date: Jun. 3, 2009; English Abstract of CN101445419.
Linde Ag, "Method for the separation of hydrocarbons in a plant," Espacenet, Publication Date: Mar. 30, 2011, English Abstract of CN101993322.
International Search Report for PCT/EP2012/003299 dated Oct. 5, 2012.
Linde Ag, "Method for the separation of hydrocarbons in a plant for producing hydrocarbon from a hydrocarbon-containing element by splitting, comprises compressing and drying the product gas of splitting containing gaseous hydrocarbon material," Espancenet, Publication Date: Mar. 3, 2011; English Abstract of DE-102009038456.
English Translation of Office Action for related Chinese Patent Application No. 201280039198.3 dated Aug. 2, 2012.
Thomson Innovation Record View, English Abstract of DE-102009038456, Publication Date: Mar. 3, 2011.

* cited by examiner

SEPARATION SEQUENCE FOR HYDROCARBONS FROM A GENTLE THERMAL CLEAVAGE

The invention relates to a method for separating hydrocarbons in a facility for generating hydrocarbons from a liquid hydrocarbonaceous feed by cleavage
  wherein the product gas of the cleavage which is formed as raw gas and contains gaseous hydrocarbons is compressed and dried,
  and is conducted as feedstock into a separation stage (hereinafter: front end C3/C4 separation)
  in which the raw gas is separated into a hydrocarbon fraction of hydrocarbons having a maximum of 3 carbon atoms and a hydrocarbon fraction of hydrocarbons having at least 4 carbon atoms,
  wherein the front end C3/C4 separation comprises in terms of the process a C4 absorber and a depropanizer,
  wherein a hydrocarbon fraction of hydrocarbons having a maximum of 3 carbon atoms is obtained as a gaseous overhead product of the C4 absorber,
  and wherein a liquid hydrocarbon fraction of hydrocarbons having at least 4 carbon atoms is obtained as a bottom product of the depropanizer.

In a facility for generating hydrocarbons, what is termed an olefin plant, the hydrocarbons or olefins are generated by cleaving hydrocarbonaceous feeds. The hydrocarbonaceous feeds in this case are either in the liquid or gaseous phase and are converted by thermal or catalytic cleavage with or without steam into relatively short-chain hydrocarbons. The mixture of predominantly relatively short-chain olefins formed in the cleavage is termed cracked gas or raw gas. In the cleavage of a liquid hydrocarbonaceous feed, the raw gas is mostly conducted as feed into an oil scrubber. In the oil scrubber the raw gas is cooled and remaining relatively long-chain hydrocarbons, such as coke particles and heavy oil components, for example, are scrubbed out of the raw gas.

Subsequently the raw gas is conducted into a water scrubber for further purification and cooling and compressed in the raw gas compressor. In the cleavage of a gaseous hydrocarbonaceous feed, usually the oil scrubbing can be dispensed with. Subsequently, the raw gas is freed from further contaminants such as carbon dioxide and hydrogen sulfide in a lye scrubber of the prior art, and dried.

The purified and dried raw gas then consists of a mixture of desired olefin products and byproducts. In order to be able to utilize the desired olefin products, the mixture must be separated into the individual olefin components.

Such a method for separating hydrocarbons starts, according to the prior art, either with a separation stage in which olefins having at most 2 carbon atoms are separated from olefins having at least 3 carbon atoms (front end $C_2/C_3$ separation), or a separation stage in which olefins having at most 3 carbon atoms are separated from olefins having at least 4 carbon atoms (front end $C_3/C_4$ separation).

If the separation sequence begins with a front end $C_2/C_3$ separation, the resultant olefin fraction having at most 2 carbon atoms ($C_2$ fraction), after a catalytic hydrogenation for removal of acetylene, is passed to a low-temperature fractionation part where it is fractionated into the individual fractions thereof. The $C_2$ fraction is separated here from the methane and hydrogen fraction. The remaining fraction of hydrocarbons having at least 3 carbon atoms ($C_{3+}$ fraction) is conducted into a separation stage (depropanizer) in which the bottom product obtained is a fraction of hydrocarbons having at least 4 carbon atoms ($C_{4+}$ fraction). In the depropanizer, an olefin fraction of hydrocarbons having 3 carbon atoms ($C_3$ fraction) is obtained overhead. The $C_3$ fraction is then likewise catalytically hydrogenated before further processing thereof.

In the context of this application, a hydrocarbon fraction which consists of hydrocarbons that have n carbon atoms is termed a $C_n$ fraction. If this hydrocarbon fraction consists of hydrocarbons that have at least n carbon atoms, the hydrocarbon fraction is termed a $C_{n+}$ fraction. A fraction of hydrocarbons having a maximum of n carbon atoms is termed a $C_{n-}$ fraction. Here, n indicates the natural numbers 1, 2, 3, 4 . . . .

A separation stage in which hydrocarbons having 2 or more carbon atoms are obtained as a liquid bottom product is termed a demethanizer in the context of this application. A separation stage having a $C_{3+}$ fraction as bottom product is termed a deethanizer. Correspondingly, a separation stage having a $C_{4+}$ bottom fraction is termed a depropanizer.

In a separation sequence of the prior art which begins with a front end $C_3/C_4$ separation, a $C_3$ fraction and a $C_{3+}$ fraction are obtained at the pressure of the compressed raw gas. At the prevailing full raw gas pressure, sharp separation into a $C_{3-}$ fraction and a $C_{4+}$ fraction is not possible according to the prior art, since the bottom temperature would be so high that increased polymer formation and thus undesired deposit formation would occur. In the further separation sequence of the prior art, the $C_{3-}$ fraction, after a catalytic hydrogenation, is conducted to a $C_2/C_3$ separation. The $C_{3-}$ fraction is separated into a $C_3$ fraction and a $C_{2-}$ fraction. The $C_{4+}$ fraction is passed to a $C_3/C_4$ separation where it is separated into a $C_3$ fraction and a $C_{4+}$ fraction and the resultant $C_3$ fraction must then be catalytically hydrogenated.

Therefore, according to the prior art, not only in a separation sequence having a front end $C_2/C_3$ separation but also in a separation sequence having a front end $C_3/C_4$ separation, 2 independent catalytic hydrogenation stages with the corresponding tubular and fixed-bed reactor are necessary.

DE 102006010519 proposes an alternative method for separating olefins. DE 102006010519 discloses a separation sequence having a $C_4$ absorber operating at full raw gas pressure and a depropanizer which is operated at a pressure of 8-12 bar. The combination of $C_4$ absorber and depropanizer separates the olefins into a $C_{3-}$ fraction and a $C_{4+}$ fraction. The $C_{3-}$ fraction is then completely compressed and conducted for catalytic hydrogenation, whereas the $C_{4+}$ fraction is removed for further processing. The $C_{3-}$ fraction, after the catalytic hydrogenation, is subjected to a $C_2/C_3$ separation and separated into a $C_{2-}$ fraction and a $C_3$ fraction. The $C_{2-}$ fraction is passed on as feed into the low-temperature separation part, while the $C_3$ fraction is conducted for further processing.

A similar separation sequence for a liquid hydrocarbonaceous feed is described in DE 102009038456. In the separation sequence disclosed here, likewise a $C_4$ absorber is combined with a depropanizer, wherein the $C_4$ absorber is operated at full raw gas pressure and the depropanizer is operated at a pressure between 8 bar and 12 bar. The $C_{3-}$ fraction, after the catalytic hydrogenation, is subjected to a $C_2/C_3$ separation, wherein the $C_{3-}$ fraction is separated in a first column into a $C_{2-}$ fraction and a $C_2/C_3$ fraction. The further separation proceeds in a second column having two sections which are separated in terms of the process, wherein the upper section is constructed as a demethanizer and the lower section as a deethanizer. In the demethanizer, dissolved methane and dissolved hydrogen are stripped out of the condensates of the low temperature cooling. In the deethanizer, a $C_{2-}$ fraction and a $C_3$ fraction are formed. The $C_3$ fraction C3 is obtained here as a bottom product. A part of the liquid $C_2$ fraction from the demethanizer serves as reflux. The bottom of the deethanizer is boiled up either with raw gas or with warm $C_3$ refrigerant or with warm mixed refrigerant. The $C_2$ fractions from the second column which are withdrawn as gaseous and liquid product laterally from the bottom of the demethanizer of the second column are applied to a $C_2$ splitter. There, ethylene is obtained as an overhead product.

The object of the present invention is to design a method of the type stated at the outset in such a manner that the expenditure on energy and apparatus for separating hydrocarbons is minimized. In this case, in particular, expenditure on energy is to be minimized in the separation of a raw gas formed in cleavage which has a ratio of ethylene to propylene of virtually 1, in particular less than 1.

The object in question is achieved by a method for separating hydrocarbons generated from cleavage of a hydrocarbonaceous feed:
wherein the raw gas formed by the cleavage contains gaseous hydrocarbons and is compressed and dried,
the raw gas in then fed as a feedstock into a front end C3/C4 separation stage,
the raw gas is separated in the C3/C4 separation stage into a hydrocarbon fraction of hydrocarbons having a maximum of 3 carbon atoms and a hydrocarbon fraction of hydrocarbons having at least 4 carbon atoms,
wherein the front end C3/C4 separation comprises a C4 absorber and a depropanizer,
wherein the hydrocarbon fraction of hydrocarbons having a maximum of 3 carbon atoms is obtained as a gaseous overhead product of the C4 absorber,
wherein the hydrocarbon fraction of hydrocarbons having at least 4 carbon atoms is obtained as a bottom liquid product of the depropanizer, and characterized in that
wherein the front end C3/C4 separation further comprises a C2/C4 separation stage arranged between C4 absorber and depropanizer.

According to the invention, the separation sequence of the hydrocarbon products of the raw gas begins with a front end C3/C4 separation which comprises a further C2/C4 separation stage in terms of the process. This further C2/C4 separation stage is arranged between the C4 absorber and the depropanizer.

At a relatively high fraction of relatively long-chain hydrocarbons in the raw gas, i.e. specifically for a raw gas having a high $C_{4+}$ fraction, during compression of the raw gas, not only does the amount of condensate increase, but also the fraction of the dissolved $C_{2-}$ components in the condensates, in such a manner that a sharp front end C3/C4 separation becomes more difficult and more expensive energetically. However, this problem is completely solved by the present invention. By means of the additional C2/C4 separation stage, the refrigeration requirement, especially of the overhead product of the depropanizer, is decreased, and thus the energy expenditure of the separation sequence is minimized.

According to the invention, a further C2/C4 separation stage is arranged between the C4 separator and the depropanizer. In this separation stage, $C_{2-}$ components and $C_{4+}$ components are separated, wherein the $C_3$ components in this separation stage are situated not only in the gaseous overhead, but also in the liquid bottom product, in such a manner that the overhead gas of this separation stage can be condensed at a relatively high temperature level. As a result, a temperature elevation in a range of increased polymer formation is avoided in the bottom product.

The entire front end C3/C4 separation according to the invention consisting of the C4 absorber, the C2/C4 separation stage and the depropanizer permits overall a sharp separation in terms of the process into a $C_{3-}$ fraction and a $C_{4+}$ fraction of the raw gas that is formed in the cleavage and then compressed. In this case, the temperatures are held continuously in ranges at which no polymer formation or deposit formation occurs. Owing to the combination according to the invention of the C4 absorber, the C2/C4 separation stage and the depropanizer, and also owing to non-sharp separation, successively the pressure of the resulting condensates can be reduced during the separation process to the extent that in the depropanizer a $C_{4+}$ fraction occurs which does not contain hydrocarbons having less than four carbon atoms, without in this case the bottom temperature increasing in such a manner that polymer formation or deposit formation occurs, and wherein the energetic expenditure for separation is minimized.

In a preferred embodiment of the invention, the C4 absorber and the C2/C4 separation stage are operated at a pressure between 18 bar and 20 bar, wherein preferably the C2/C4 separation stage is operated at a somewhat higher pressure than the C4 absorber. This embodiment of the invention permits the compressed raw gas to be applied directly to the C4 absorber at full raw gas pressure.

In a preferred embodiment of the invention, the C4 absorber and the C2/C4 separation stage are combined in one column. In this embodiment, C4 absorber and C2/C4 separation stage are combined in one column, but form sections of this column which are separated in terms of the process. Correspondingly, the pressure level of both processing sections (C4 absorber, C2/C4 separation stage) in this embodiment of the invention is identical.

In an alternative embodiment of the invention, the C4 absorber and the C2/C4 separation stage are different columns. In this alternative embodiment of the invention, the C4 absorber and the C2/C4 separation stage which are clearly separated in terms of the process are also divided in terms of apparatus into two separate columns. In this embodiment of the invention, a bottom pump is required for the C4 absorber. The C2/C4 separation stage is operated at a somewhat higher pressure than the C4 absorber.

Advantageously, the bottom product of the C2/C4 separation stage is applied to the depropanizer. The C2/C4 separation stage separates the hydrocarbons into a $C_{3-}$ fraction and a $C_{3+}$ fraction. The $C_{3+}$ fraction in this case arises as a bottom product. This bottom product is advantageously applied to the depropanizer, where the $C_3$ fraction is separated off and a pure $C_{4+}$ fraction is obtained as bottom product.

The depropanizer is preferably operated at a pressure between 10 and 12 bar.

Particularly preferably, the raw gas that is to be separated contains ethylene and propylene in a ratio of 1.5 or less than 1. In this process, the conditions of cleavage are set correspondingly. The advantages of the invention are particularly expressed when the conditions of the cleavage are set in such a manner that the propylene fraction in the raw gas corresponds to the ethylene fraction or is greater than the ethylene fraction. However, when the propylene fraction is less than the ethylene fraction, but higher than is usual, the advantages of the invention are also expressed in an excellent manner. In such a raw gas, the invention succeeds in particular by carrying out a front end $C_3/C_4$ separation in a sharp manner, without polymer formation or deposit formation occurring in the apparatuses that participate.

A characteristic variable in the generation of unsaturated hydrocarbons by means of cleavage is what is termed cracking sharpness. The cracking sharpness is indicated by the ratio of propylene to ethylene. The cracking sharpness depends primarily on the temperature of the cracked gas at the cracking furnace exit, the residence time in the cracking furnace and the exact composition of the feed. The advantages of the invention are displayed particularly under mild cracking conditions, that is to say at a propylene to ethylene ratio from 0.65 to 1.5 kg/kg, preferably from 0.7 to 1.3 kg/kg, particularly preferably from 0.8 to 1.2 kg/kg.

Preferably, a ratio of ethylene to propylene or of propylene to ethylene, as is stated in the two preceding paragraphs, is achieved in that, before the thermal cleavage, a certain fraction of saturated hydrocarbons (preferably between 3% by weight and 40% by weight, particularly preferably between 5% and 30% by weight, in particular between 15% and 25% by weight) is admixed to the liquid hydrocarbonaceous feed substantially consisting of saturated hydrocarbons. The thermal cleavage takes place here expediently under mild conditions (preferably from 700° C. to 800° C., further preferably from 720° C. to 790° C., particularly preferably from 740° C. to 780° C., for example 740° C.-800° C., and/or 2.5 bar abs-4 bar abs). Advantageously, in this case, one or more returned $C_{4+}$ fractions are admixed as saturated hydrocarbons to the liquid feed.

The present invention is particularly suitable for separating hydrocarbons in a facility for generating hydrocarbons from a liquid hydrocarbonaceous feed by cleavage.

With the present invention, it is possible in particular to minimize the expenditure in terms of energy of a separation sequence for a raw gas, as is formed, in particular, in the cleavage of liquid hydrocarbonaceous feeds. Especially in a raw gas having a relatively high $C_{4+}$ fraction, in the front end C3/C4 separation according to the invention, sharp separation into a $C_{3-}$ fraction and a $C_{4+}$ fraction of the raw gas can be achieved without elevated polymer formation or deposit formation occurring in the apparatuses that participate.

Hereinafter, the invention will be described in more detail with reference to both exemplary embodiments shown in FIGS. 1 and 2.

BRIEF DESCRIPTION OF DRAWINGS

FIG. 1 shows an embodiment of the method according to the invention for separating hydrocarbons in a facility in which a liquid hydrocarbonaceous feed is cleaved in such a manner that the raw gas formed in the cleavage has an ethylene to propylene fraction of a maximum of 1 or less. The raw gas 1 formed as cleavage product is conducted as feed into an oil scrubber (which is not shown). In the oil scrubber the raw gas is cooled and remaining relatively long-chain hydrocarbons, such as coke particles and heavy oil components, for example, are separated out of the raw gas. Subsequently, the raw gas 1 is conducted into a water scrubber (which is not shown) for further purification and cooling and conducted from there into a three-stage raw gas compression 2a. In the three-stage raw gas compression 2a, the raw gas is compressed to a pressure of approximately 20 bar, preferably 19 bar, and freed in a scrubber 3 from acid gas components such as carbon dioxide and hydrogen sulfide. Subsequently, the purified raw gas is precooled in a precooler 4 and dried via the two dryers 5a and 5b. The actual separation sequence of the raw gas 1 then begins.

Figure 1:
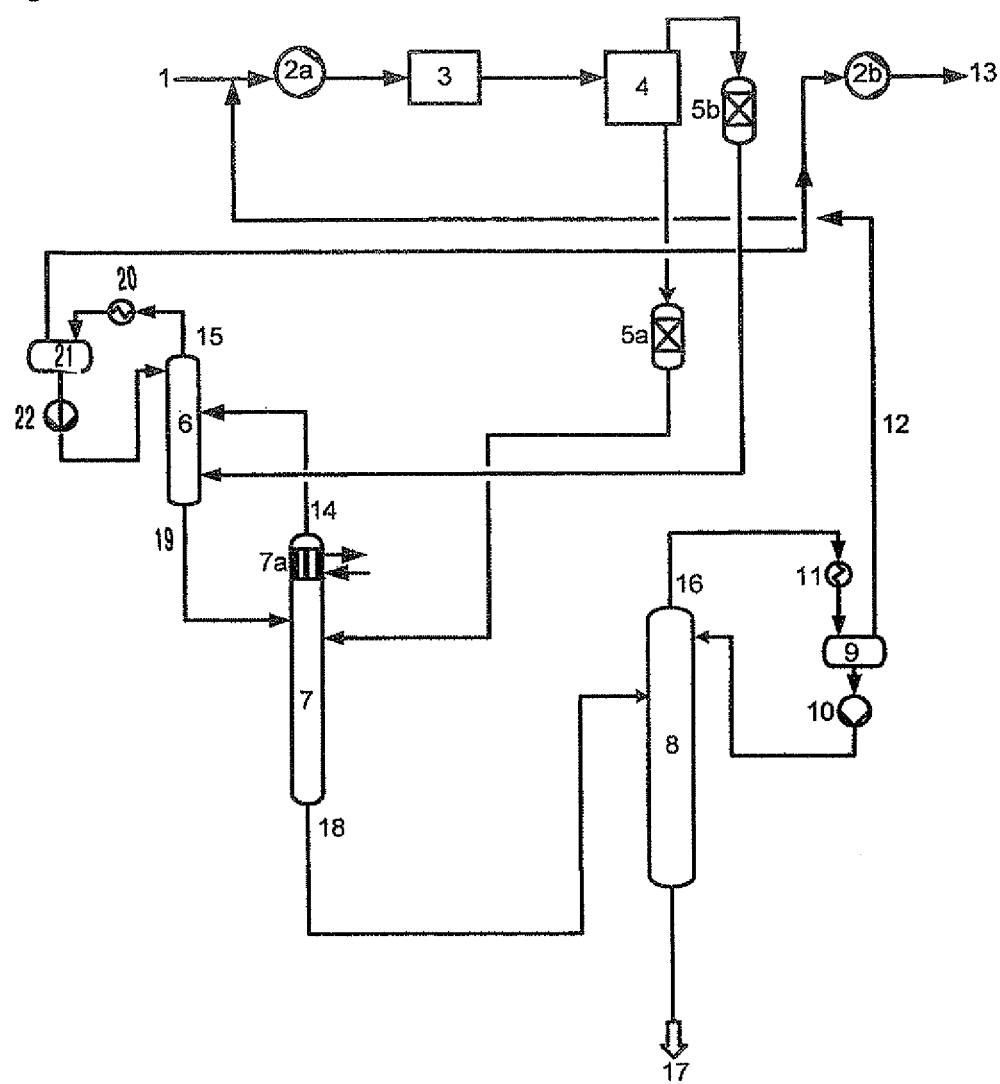
FIG. 1 shows an embodiment of the invention in which C4 absorber and C2/C4 separation stage are different columns.

As a result of the raw gas compression 2a, the raw gas is heated in such a manner that cooling is necessary before the acid gas scrubber 3 (which is not shown). The resultant condensate is conducted directly into the depropanizer 8 (which is not shown). The acid gas components that are necessarily fed in this case to the depropanizer 8, however, leave the depropanizer 8 with the gas phase 16 overhead and are returned 12 to the raw gas compression 2a. The condensates depicted in this section can be withdrawn in this case from each stage of the raw gas compression 2a, but preferably, as in this exemplary embodiment, after the third stage of the raw gas compression 2a.

The condensate that is formed in the precooling 4 is applied via the dryer 5a to the C2/C4 separation stage 7. The overhead gas formed in the precooling 4 is applied via the dryer 5b directly to the C4 absorber 6. Both the C4 absorber 6 and the C2/C4 separation stage 7 operate in this case at the full raw gas pressure between 18 and 20 bar, preferably 19 bar. The pressure in the C4 absorber 6 is slightly less than the pressure in the C2/C4 separation stage 7. In the C4 absorber 6, a pure $C_{3-}$ fraction 15 is formed as gaseous overhead product. This is further compressed in a fourth compression stage 2b and conducted for further fractionation 13, in which then the valuable products ethylene and propylene are separated out from this $C_{3-}$ fraction 15.

The bottom product 19 of the C4 absorber 6 and the condensate from the dryer 5a are introduced into the C2/C4 separation stage 7. In the C2/C4 separation stage 7, the hydrocarbons having three carbon atoms are distributed over the gaseous overhead product and the liquid bottom product. In this case, the overhead product only contains few hydrocarbons having more than three atoms, and the bottom product is free from hydrocarbons having fewer than two carbon atoms. Therefore, in the C2/C4 separation stage 7, a gaseous overhead product is obtained which is a C4 fraction 14. The liquid bottom product 18 of the C2/C4 separation stage 7 is a C3+ fraction 18. In order to ensure that the overhead product 14 of the C2/C4 separation stage 7 contains only few hydrocarbons having four or more carbon atoms, the C2/C4 separation stage 7 has a top condenser 7a.

The bottom product 18 of the C2/C4 separation stage 7 is applied to the depropanizer 8 for separating off the $C_{4+}$ fraction. The depropanizer 8 operates at a pressure between at 8 and 12 bar. The bottom product 18 of the C2/C4 separation stage 7 is therefore expanded into the depropanizer 8. In the depropanizer 8, a pure $C_{4+}$ fraction forms as bottom product 17 and is withdrawn therefrom. The bottom product 17 of the depropanizer is free in this case from any $C_{3-}$ components. As overhead product 16 of the depropanizer, a fraction is obtained which principally consists of hydrocarbons having three carbon atoms. Via a heat exchanger 11, the overhead product 16 of the depropanizer 8 is further cooled and conducted into a separator 9. The gas phase 12 obtained in the separator is returned to the raw gas 1 upstream of the three-stage compression 2a. The liquid product of the separator 9 is applied via a pump 10 as reflux to the depropanizer 8.

Likewise, the gaseous overhead product 15 of the C4 absorber 6 is cooled via a heat exchanger 20 and conducted into a separator 21. The liquid phase formed in this case is applied again as reflux via the pump 22 to the C4 absorber 6. The gaseous phase is compressed in the fourth stage of the raw gas compression 2b and conducted as C$_{3-}$ fraction to the ethylene and propylene production 13.

Figure 2:
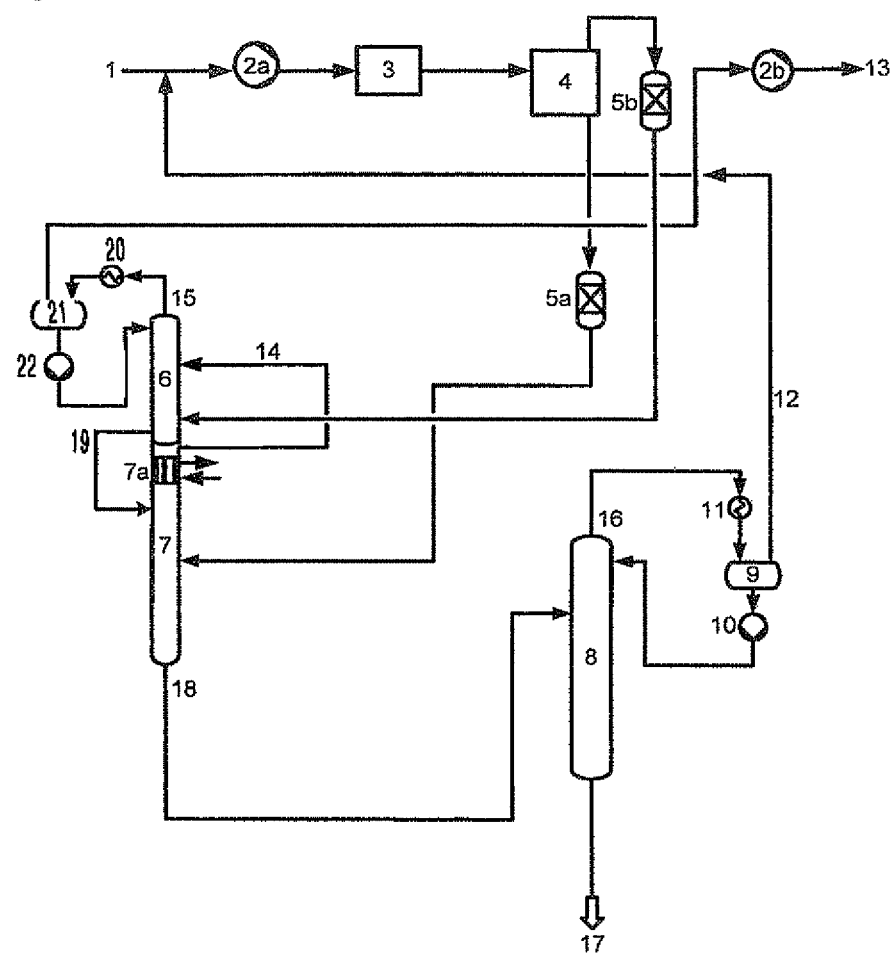
FIG. 2 shows an alternative embodiment of the invention in which C4 absorber and C2/C4 separation stage are arranged in one column.

FIG. 2 functions in a similar manner to the exemplary embodiment as per FIG. 1. The same parts have been labeled with the same reference signs as in FIG. 1. In contrast to the exemplary embodiment as per FIG. 1, however, here C4 absorber 6 and C2/C4 separation stage 7 are arranged in one column.

The invention claimed is:

1. A method for separating hydrocarbons generated from a hydrocarbonaceous feed by cleavage, wherein said method comprises:
    compressing (2a) and drying (5a, 5b) a raw gas (1) from the cleavage of said hydrocarbonaceous feed, said raw gas (1) containing gaseous hydrocarbons,
    introducing said raw gas (1) into a front end C3/C4 separation stage,
    separating the raw gas (1) in said front end C3/C4 separation stage into a hydrocarbon fraction of hydrocarbons having a maximum of 3 carbon atoms (15) and a hydrocarbon fraction of hydrocarbons having at least 4 carbon atoms (17), said front end C3/C4 separation stage comprises a C4 separator (6), a depropanizer (8), and a C2/C4 separation stage (7),
    removing a bottom product stream from said C4 separator (6) and introducing said bottom product stream into said C2/C4 separation stage (7), and
    removing a liquid stream (18) from said C2/C4 separation stage (7) and introducing said liquid stream into said depropanizer (8),
    wherein said hydrocarbon fraction of hydrocarbons having a maximum of 3 carbon atoms is obtained as a gaseous overhead product (15) from said C4 separator (6),
    wherein said hydrocarbon fraction of hydrocarbons having at least 4 carbon atoms is obtained as a bottom liquid product (17) from said depropanizer (8), and
    wherein said C2/C4 separation stage (7) is operated at a higher pressure than said C4 separator (6).

2. The method as claimed in claim 1, wherein said C2/C4 separation stage (7) is a C2/C4 separation column (7), and said C4 separator (6) and said C2/C4 separation column (7) are operated at a pressure between 18 bar and 20 bar.

3. The method as claimed in claim 1, wherein said C4 separator (6) and said C2/C4 separation stage (7) are combined in one column.

4. The method as claimed in claim 3, further comprising removing an overhead stream from said C2/C4 separation stage (7) and introducing said overhead stream into said C4 separator (6).

5. The method as claimed in claim 4, wherein said C2/C4 separation stage (7) has a top condenser.

6. The method as claimed claim 1, wherein said C4 separator (6) and said C2/C4 separation stage (7) are different columns.

7. The method as claimed in claim 6, further comprising removing an overhead stream from said C2/C4 separation stage (7) and introducing said overhead stream into said C4 separator (6).

8. The method as claimed in claim 7, wherein said C2/C4 separation stage (7) has a top condenser.

9. The method as claimed in claim 1, wherein said depropanizer (8) is operated at a pressure between 10 bar and 12 bar.

10. The method as claimed in claim 1, wherein said raw gas (1) contains ethylene and propylene at an ethylene to propylene weight ratio of 1.5 or less than 1.

11. The method as claimed in claim 1, wherein the cleavage is performed under conditions to achieve a propylene to ethylene ratio from 0.65 to 1.5 kg/kg.

12. The method as claimed in claim 1, wherein the cleavage is performed under conditions to achieve a propylene to ethylene ratio from 0.7 to 1.3 kg/kg.

13. The method as claimed in claim 1, wherein the cleavage is performed under conditions to achieve a propylene to ethylene ratio from 0.8 to 1.2 kg/kg.

14. The method as claimed in claim 1, further comprising,
    after said compressing (2a) of the raw gas and prior to said drying (5a, 5b) of the raw gas, subjecting said raw gas to a precooling stage,
    removing a condensate and overhead gas from said precooling and separately sending said condensate and overhead gas to said drying (5a, 5b), and
    thereafter sending said overhead gas to said C4 separator (6), and sending said condensate to said C2/C4 separation stage (7).

15. The method as claimed in claim 14, further comprising
    removing an overhead stream from said C2/C4 separation stage (7) and introducing said overhead stream into said C4 separator (6).

16. The method as claimed in claim 1, further comprising removing an overhead stream from said C2/C4 separation stage (7) and introducing said overhead stream into said C4 separator (6).

17. A method for separating hydrocarbons generated from a hydrocarbonaceous feed by cleavage, wherein said method comprises:
    compressing (2a) and drying (5a, 5b) a raw gas (1) from the cleavage of said hydrocarbonaceous feed, said raw gas (1) containing gaseous hydrocarbons,
    introducing said raw gas (1) into a front end C3/C4 separation stage, and
    separating the raw gas (1) in said front end C3/C4 separation stage into a hydrocarbon fraction of hydrocarbons having a maximum of 3 carbon atoms (15) and a hydrocarbon fraction of hydrocarbons having at least 4 carbon atoms (17),
    wherein the front end C3/C4 separation stage comprises a C4 separator (6) and a depropanizer (8),
    wherein said hydrocarbon fraction of hydrocarbons having a maximum of 3 carbon atoms is obtained as a gaseous overhead product (15) from said C4 separator (6),
    wherein said hydrocarbon fraction of hydrocarbons having at least 4 carbon atoms is obtained as a bottom liquid product (17) from said depropanizer (8),
    wherein the front end C3/C4 separation stage further comprises a C2/C4 separation stage (7),
    wherein the C2/C4 separation stage (7) is arranged between said C4 separator (6) and said depropanizer (8), and wherein a stream from a bottom region of said C4 separator (6) is introduced into said C2/C4 separation stage (7), and a stream from a bottom region of said C2/C4 separation stage (7) is introduced into said depropanizer (8), and
    wherein said C2/C4 separation stage (7) is operated at a higher pressure than said C4 separator (6).

* * * * *